United States Patent [19]
Ren

[11] Patent Number: 6,086,970
[45] Date of Patent: *Jul. 11, 2000

[54] LUBRICIOUS SURFACE EXTRUDED TUBULAR MEMBERS FOR MEDICAL DEVICES

[75] Inventor: Brooke Q. Ren, Champlin, Minn.

[73] Assignee: SciMed Life Systems, Inc., Maple Grove, Minn.

[*] Notice: This patent issued on a continued prosecution application filed under 37 CFR 1.53(d), and is subject to the twenty year patent term provisions of 35 U.S.C. 154(a)(2).

[21] Appl. No.: 09/067,834

[22] Filed: Apr. 28, 1998

[51] Int. Cl.$^7$ .......................... A61M 25/00; A61M 5/32; B65D 1/40; B29D 22/00
[52] U.S. Cl. .................. 428/36.9; 428/36.92; 264/209.1; 264/211; 508/449; 604/96; 604/265
[58] Field of Search .............................. 604/265, 96, 194, 604/508, 915; 428/36.9, 36.91, 36.92; 508/106, 449, 450, 451; 252/367.1, 182.12; 208/20; 264/464, 472, 513, 516, 209.1, 211

[56] References Cited

U.S. PATENT DOCUMENTS

| | | | |
|---|---|---|---|
| 2,998,397 | 8/1961 | Riesing | 260/17 |
| 3,287,288 | 11/1966 | Reiling | 260/4 |
| 3,871,200 | 3/1975 | Onoda et al. | 72/41 |
| 3,908,038 | 9/1975 | Nienart et al. | 427/27 |
| 3,994,814 | 11/1976 | Cairns | 252/12.6 |
| 4,159,286 | 6/1979 | Khattab et al. | 260/857 UN |
| 4,334,037 | 6/1982 | Allen | 525/199 |
| 4,596,839 | 6/1986 | Peters | 523/175 |
| 4,647,602 | 3/1987 | Wilczak et al. | 523/204 |
| 4,714,740 | 12/1987 | Lee et al. | 525/179 |
| 4,810,733 | 3/1989 | Sakuma et al. | 523/206 |
| 4,945,126 | 7/1990 | Crosby et al. | 524/507 |
| 4,962,136 | 10/1990 | Peters | 523/220 |
| 5,085,649 | 2/1992 | Flynn | 604/282 |
| 5,091,205 | 2/1992 | Fan | 427/2 |
| 5,232,644 | 8/1993 | Hammond et al. | 264/73 |
| 5,399,598 | 3/1995 | Peters | 524/68 |
| 5,418,270 | 5/1995 | Peters | 524/406 |
| 5,565,417 | 10/1996 | Salvia | 508/167 |
| 5,645,603 | 7/1997 | Peters | 623/20 |
| 5,712,229 | 1/1998 | Hopkins et al. | 508/202 |

FOREIGN PATENT DOCUMENTS

| | | |
|---|---|---|
| WO 96/03163 A1 | 2/1996 | WIPO . |
| WO 96/34635 A2 | 11/1996 | WIPO . |
| WO96/34635 | 11/1996 | WIPO . |

OTHER PUBLICATIONS

Sekutowski, "Fillers, Extenders, and Reinforcing Agents," *Plastics Additives and Modifiers Handbook*, Chapter 35, pp. 493–497.

"Fluid–film Lubrication," Britannica Online, Internet Address <http://www.eb.com>, accessed Sep. 28, 1997, seven pages.

"Stearic Acid," Britannica Online, Internet Address <http://www.eb.com>, accessed Sep. 28, 1997, one page.

"Surface Coatings," Britannica Online, Internet Address <http://www.eb.com>, accessed Sep. 28, 1997, three pages.

"Advanced Inorganic Chemistry" Fifth Edition bu F.A. Cotton and G. Wilkinson, John Wiley & Sons, p. 809, 1988.

*Primary Examiner*—Ellis Robinson
*Assistant Examiner*—John J. Figueroa
*Attorney, Agent, or Firm*—Crompton, Seager & Tufte, LLC

[57] ABSTRACT

A catheter tube having improved strength and lubricity. The catheter tube can be used advantageously as a guide wire tube for small profile intravascular catheters. The tube can be formed by extruding a mixture of thermoplastic polymeric material, hard particles, lubricating particles, and a lubricant. The lubricant is preferably an external lubricant capable of forming a film over the tube surfaces. One tube is formed of polyamide, molybdenum disulfide particles, PTFE particles, and zinc stearate. Applicants believe the hard disulfide particles and lubricating PTFE particles protrude from the tubular surfaces and are coated with a film of lubricating zinc stearate. The film is believed to reduce the friction and resulting PTFE elongation caused by a guide wire sliding over the PTFE protrusions.

7 Claims, No Drawings

LUBRICIOUS SURFACE EXTRUDED TUBULAR MEMBERS FOR MEDICAL DEVICES

FIELD OF THE INVENTION

The present invention relates generally to tubular members for use in medical catheters. More specifically, the present invention relates to a tube composition resulting in a strong yet lubricious tube.

BACKROUND OF THE INVENTION

Coronary arteries provide blood and nutrients to the heart muscle. The arteries are subject to atherosclerosis or hardening of the arteries. Vascular regions have plaques formed within, resulting in stenosed regions having reduced cross-sectional area. The reduced area causes a reduction in transport of blood, oxygen, and nutrients which can result in angina, myocardial infarction and death.

A commonly used method for treating atherosclerosis is Percutaneous Transluminal Coronary Angioplasty (PTCA). PTCA includes insertion of a balloon catheter through an incision in the femoral artery near the groin, advancement of the balloon over the aortic arch, further advancement within the selected coronary artery, continuing until the balloon portion is placed across the stenosed region. The balloon is inflated, widening the narrowed vessel region.

Smaller arteries branch off the main coronary arteries, becoming narrower and traversing a more tortuous path. Catheters having smaller profiles or transverse cross-sectional areas are better suited to reach and treat these narrower, more distant arteries. Balloon catheters having smaller distal profiles are better able to facilitate the balloon carrying distal end in crossing a narrowed, stenosed vessel region. Once across the stenosis, balloon expansion can dilate the stenosis. For these and other reasons, reducing the profile of catheters has long been important in catheter design.

Catheter tubes, including guide wire tubes, have been made of polyethylene, often high density polyethylene (HDPE). The polyethylene used is reasonably lubricious, but is not as strong as some other polymers. Tubes formed of polyethylene could be designed to required strengths by utilizing sufficiently thick tube walls. Thicker tube walls, however, increase tube and catheter profile. As previously discussed, smaller profiles and tube walls are desirable. Small profile catheters typically have thinner walls which results in lower collapse pressures, the pressure at which tube walls collapse inward. Collapse pressure is an important design criteria for guide wire tubes. Thinner tube walls also result in lower burst strength, an important property of inflation tubes. In catheters having guide wire and inflation lumen walls formed from the same material, burst and collapse pressures arc both affected by material selection.

To achieve improved or adequate collapse and burst pressures while using thin-walled tubing, other polymers such as polyamide (PA) have been used. Polyamidc has higher burst and collapse pressures than HDPE, but also a higher coefficient of friction (COF). This reduces the mobility of a guide wire within the lumen of these tubular members. Fluoropolymers such as polytetrafluoroethylene (PTFE) are highly lubricious and have been used to line guide wire tubes. PTFE, however, is very difficult to extrude as the melting temperature is high and the viscosity of the polymer melt is extremely high. In an attempt to lower the coefficient of friction while maintaining the higher burst and collapse pressures, the incorporation of PTFE particles within thermoplastic has been discussed. PCT publication WO 9603163 A1 proposes including finely divided fluoropolymer particles in an extruded polyester catheter tube.

Applicants have discovered that the strength and lubricity of tubes formed of mixtures of PTFE particles within polyamide have been less than desirable, causing significantly higher friction than expected.

What would be desirable and has not heretofore been provided is a catheter tube having high lubricity as well as high burst and collapse pressures.

SUMMARY OF THE INVENTION

The present invention includes strong, thin-walled, lubricious catheter tubes which do not compromise burst and collapse pressures and methods for making same. Catheter tubes according to the present invention can be used advantageously as guide wire tubes. Guide wire tubes make use of the improved lubricity and collapse strength of the present invention, while maintaining a lower profile with a thin wall. Catheter tubes made according to the present invention include a polymer material, hard particles, lubricating particles, and external lubricant, all of which are blended together prior to extrusion. The catheter tubes are preferably extruded, the polymers being thermoplastic polymers capable of being melt processed, mixed with other materials, and extruded. Hard particles, lubricating particles, and external lubricant can be mixed with polymer resin, heated, melted, and extruded using extruders well known in the art. Catheter tubes according to the present invention can be free-extruded or extruded over wires or mandrels, the wires or mandrels later being removed, leaving a small lumen thin-walled tube having a tightly controlled inside diameter.

One thermoplastic polymer suitable for use in the present invention is polyamide. Suitable hard particles for inclusion in the polymer melt include molybdenum disulfide. Lubricating particles used in the catheter tubes of the present invention include PTFE. External lubricants are those lubricants included with the polymer prior to extrusion that have a tendency to migrate towards the tube surfaces when the polymer is extruded, and can form an external film over the tube. One external lubricant is zinc stearate.

One preferred catheter tube is formed of polyamide polymer, PTFE lubricious particles, molybdenum disulfide hard particles, and zinc stearate external lubricant. In this tube, PTFE has an average particle size of about 0.5 micron and is present in a concentration of about 5%. The molybdenum disulfide in this embodiment has an average particle size between about 0.3 and about 40 microns and is present in a concentration of about 5%. Zinc stearate is present in a concentration of about 2% in this embodiment.

DETAILED DESCRIPTION OF THE PREFERRED EMBODIMENTS

The present invention includes a polymeric tube which is a composite formed at least in part from polymeric material, hard particles, lubricating particles, and external lubricant. The tube is preferably extruded from a mixture having a thermoplastic polymer, hard particles, lubricating particles and external lubricant. The constituent materials are preferably mixed prior to extrusion and initially extruded as a substantially homogeneous mixture.

Many thermoplastics are suitable for use in the present invention. The particular thermoplastic may be selected based on strength, flexibility and lubricity properties. Examples of polymers believed suitable include polyethylene, polyamide, polyester, fluoropolymer, and copolymers or blends thereof. A preferred polymer is polyamide. Pure polyamide has high strength properties, such as burst and collapse pressure, but less than ideal lubricity.

Lubricating solids are preferably incorporated into the polymer mixture prior to extrusion. Preferred lubricating solids include fluoropolymer powders. A most preferred lubricating solid is PTFE powder. The lubricating solid preferably has an average size in the range of about 0.1 micron to about 1 micron. "Size", as used herein, refers to the length of the maximum dimension of a particle. One preferred particle size is about 0.5 micron. The lubricating solid preferably has a concentration no greater than about 5%. One preferred lubricating solid concentration is about 5%.

A preferred composition includes polyamide and PTFE particles. Applicants have found that such combination, alone, results in a tube having a collapse pressure less than polyamide alone and a friction force ratio (resistance to sliding as detailed below) significantly greater than polyamide alone. Thus, the addition of PTFE alone as a lubricating solid actually increases friction.

At a microscopic level, Applicants have found flat surfaces are not flat, but consist of an irregular array of hills and valleys. When one solid is placed in contact with another, a guide wire within a tube for example, the dominant asperities, often the peaks of the microscopic surfaces, initially come into contact with one another. The friction force is inversely proportional to the hardness of the surface asperities. With PTFE, the hardness of the PTFE particles are believed insufficient and plowing or smearing of the peaks occurs when the guide wire slides, causing an increase in friction. The hardness of the asperities should, therefore, be harder than the hardness of the polymeric matrix to increase lubricity over the polymer alone. Thus, having a rough surface composed of hard asperities will reduce the sliding friction of the two surfaces.

Examples of hard particles believed suitable for use with the present invention include silica, mica, glass bead, wollastonite, PI fine powder, talc, and molybdenum disulfide and mixtures thereof. A preferred hard particle is crystalline molybdenum disulfide. Preferably, the Mohs hardness of the particles is greater than or equal to 1, and a preferred range of particle sizes is about 0.3 to about 40 microns. A preferred concentration range is from about 2% to about 8%. A preferred concentration is about 5%.

Hard particles in combination with polymers, without more, have shown less than desirable lubricity properties. Applicants have found, however, that the addition of hard particles in combination with a lubricating solid, such as PTFE, improves lubricity over either compound added alone. For example, sample tubes extruded having polyamide, PTFE, and hard particles improved tube lubricity, relative to tubes not having the hard particles.

Lubricants can be classified into two groups for the purposes of this invention, internal and external. Internal lubricants are generally readily soluble in the polymer melt being extruded. External lubricants are generally insoluble. External lubricants tend to migrate strongly to the tube surfaces, and to form or release a uniform invisible film over the surfaces. The lubricating effect can be permanent. Lubricants believed suitable for use with the present invention include paraffin wax, non-polar polyethylene waxes, metallic soaps, fatty acid esters of glycerol, and montanic soaps and mixtures thereof. Polar polyethylene waxes are believed suitable for polyolefines. A preferred lubricant is zinc stearate metallic soap. A preferred concentration range is from about 0.1% to about 2.0%. One preferred concentration is about 2%.

Applicants have found that the addition of an external lubricant, in particular zinc stearate, to compounds having polyamide, PTFE particles, hard particles, further increases the lubricity of the tube without compromising tube integrity. A tube comprising 91% Vestamid L2101 (a polyamide available from Hüls America), 5% PTFE, 2% molybdenum disulfide and 2% zinc stearate demonstrated a higher collapse pressure than HDPE, with an even higher collapse pressure for an annealed sample. When testing lubricity by sliding guide wires in a tube of this composition it was found that friction force ratios did not differ greatly from that encountered with HDPE. Thus, the tube had a lubricity reasonably close to that of HDPE and a collapse pressure greater than HDPE and approaching that of polyamide.

The external lubricant is believed to form a film over the polyamide and lubricating particles. In particular, the external lubricant is believed to form a film over the PTFE particles protruding from the tube surfaces. A guide wire sliding within the lumen of a film coated polyamide tube is believed to contact film coated PTFE particles rather than uncoated PTFE particles. The reduced friction between guide wire and PTFE particles gives the guide wire less "grab" on the particle, resulting in less elongation or plowing of the particle. The film coated particle is believed to maintain more of the nominally spherical shape rather than be distorted into an oblong shape. The distortion of multitudinous uncoated PTFE particles by the sliding guide wire may be responsible for the greater friction force observed in tubes not having the external lubricant extruded with the PTFE and hard particles.

The use of zinc stearate alone was tested. A tube of Vestamide L2101 (a polyamide) with 2% zinc stearate was tested. However, it was found that collapse pressure was significantly reduced (250 psi versus 480 psi for Vestamide alone). Tubular integrity was, therefore, not acceptable with zinc stearate alone, yet collapse pressure increased to near equal that of polyamide alone by the addition of molybdenum disulfide and PTFE. It is believed that the combination of the three additives, PTFE, zinc stearate and molybdenum disulfide result in a combined effect to give improved lubricity with adequate collapse strength in a thin-walled tube.

TABLE I

| | | Surface and Friction | | |
|---|---|---|---|---|
| Trade Name | Generic Type (Formula) | Collapse Pressure (psi) | Friction Force Standard Reference Ratio w/HPC Wire | Friction Force Standard Reference Ratio w/ACS Wire |
| Marlex 4903 | HDPE | 340 | 1 | 1 |
| Vestamide L2101 | PA12 | >480 | not tested | 2.5 |

TABLE I-continued

Surface and Friction

| Trade Name | Generic Type (Formula) | Collapse Pressure (psi) | Friction Force Standard Reference Ratio w/HPC Wire | Friction Force Standard Reference Ratio w/ACS Wire |
|---|---|---|---|---|
| PA compound 1 | 91% Vestamide L2101-5% PTFE-2% zinc stearate-2% molysulfide | Annealed >480 Not annealed: 357 & 450 | 0.78 push 0.88 pull | 1.36 push 1.39 pull |
| PA compound 5 | 90% Vestamide L2102-2% (.5 μ)-8% PTFE (12 μ) | 437 | not tested | 4.86 push 2.39 pull |
| PA compound 8 | 70% Vestamide L2102-2% PTFE (.5 μ)-28% PTFE (12 μ) | 318 | not tested | 2.01 push 1.84 pull |
| PA compound 9 | 92% Vestamide L2101-3% PTFE (.5 μ)-5% silica | 397 | not tested | 5.86 push 6.82 pull |
| PA compound 10 | 92% Vestamide L2101-3% PTFE (.5 μ)-5% glass bead | 446 | 0.53 push 0.41 pull | 2.64 push 4.94 pull |
| PA compound 11 | 92% Vestamide L2101-3% PTFE (.5 μ)-5% talc | 456 | 1.39 push 0.77 pull | 3.98 push 5.21 pull |
| PA compound 12 | 92% Vestamide L2101-3% PTFE (.5 μ-5% wollastonite | 397 | not tested | 4.71 push 5.38 pull |
| PA compound 13 | 92% Vestamide L2101-3% PTFE (.5 μ)-5% modified morphology filler | >480 | not tested | 8.91 push 10.75 pull |
| PA compound 1A-0.0 | 92% Vestamide L2101-3% PTFE-.0% zinc stearate-5% molysulfide | not tested | not tested | 8.21 push 5.63 pull |
| PA compound 1A-0.5 | 91.5% Vestamide L2101-3% PTFE-.5% zinc stearate-5% molysulfide | not tested | not tested | 6.04 push 5.83 pull |
| PA compound 1A-1.0 | 91% Vestamide L2101-3% PTFE-1% zinc stearate-5% molysulfide | not tested | 0.85 push 0.88 pull | 1.67 push 1.38 pull |
| PA compound 1A-2.0 | 90% Vestamide L2101-3% PTFE-2% zinc stearate-5% molysulfide | not tested | not tested | 8.50 push 5.85 pull |

NOTE: Reference Ratio is sample results divided by HDPE results.

Referring to Table I, high density polyethylene (Marlex 4903 HDPE) was tested and found to have a collapse pressure of 340 PSI and defined to have friction force ratios of 1. One friction force ratio is defined to be the friction force encountered when sliding a hydrophilic coated (HPC) guide wire within a tube, divided by the friction force encountered in a HDPE tube. Another friction force ratio is defined to be the friction force encountered when sliding a non-coated (ACS) guide wire within a tube, divided by the HDPE tube friction force encountered. The HDPE tube is thus used to establish a baseline for comparison of the friction forces of other tube materials. As discussed previously, HDPE offers suitable lubricity but less than optimal collapse pressure at desired profiles and wall thicknesses. Polyamide (Vestamide L2101) offers a collapse pressure in excess of 480 PSI at desired profiles and wall thicknesses, but less than desirable lubricity.

The apparatus used for testing to achieve the above data was an artery fixture which included multiple curves, wherein the tubular member to be tested was affixed at regular repeatable points to duplicate the same curves for each test. Once the tubular member was affixed to the fixture in the predetermined curved pattern, the inner diameter or lumen of the tube was then flushed with water. The wire to perform the test, either a hydrophilically coated wire or a non-hydrophilically coated wire, as indicated in the table, was inserted into the lumen of the tubular member and pushed through the lumen so that the wire extended beyond the end of the tubing being tested. The wire was then pulled back so that the end of the wire lined up with the end of the tubular member being tested. The wire was then attached to a force gauge. The wire was then pulled back a distance of 6 inches and the peak tension was recorded. The wire was then pushed back 6 inches to its original position, and the peak compression was also recorded. This raw data was averaged and is expressed as a ratio to the same data which resulted from testing a high density polyethylene tube under the same conditions. Thus, the data gives a relative measure of friction with high density polyethylene as the reference material.

As evidenced from the data, the combination of a polyamide with a hard particle such as molybdenum disulfide, a lubricating particle such as PTFE, and zinc stearate resulted in tubular members having the structural integrity of a polyamide alone, while having the lubricity of a tubular member which is manufactured from high density polyethylene. A preferred composition includes about 2% to about 6% PTFE, about .5% to about 2% zinc stearate, and about 2% to about 5% molybdenum disulfide.

Numerous characteristics and advantages of the invention covered by this document have been set forth in the foregoing description. It will be understood, however, that this disclosure is, in many respects, only illustrative. Changes may be made in details without exceeding the scope of the invention. The invention's scope is, of course, defined in the language in which the appended claims are expressed.

What is claimed is:

1. A lubricious polymeric catheter tube comprising the tubular product of extrusion of a mixture comprising:

a thermoplastic polyamide;

hard particles selected from the group consisting of silica, mica, glass bead, wollastonite, talc, molybdenum disulfide and mixtures thereof, said hard particles having a Mohs hardness greater than or equal to 1;

polytetrafluoroethylene particles; and an external lubricant selected from the group consisting of paraffin wax, polyethylene waxes, metallic soaps, fatty acid esters of glycerol, montanic soaps, and mixtures thereof;

said tubular product having, high lubricity and high collapse pressures.

2. A lubricious polymeric catheter tube as recited in claim 1 wherein said hard particles comprise molybdenum disulfide particles.

3. A lubricious polymeric catheter tube as recited in claim 1 wherein said hard particles comprise molybdenum disulfide and said external lubricant comprises zinc stearate.

4. A lubricious polymeric catheter tube as recited in claim 3 wherein said molybdenum disulfide has an average particle size in the range of about 0.3 micron to about 40 microns and a concentration in the range of about 2% to about 8%.

5. A lubricious polymeric catheter tube as recited in claim 3 wherein said polytetrafluoroethylene particles have an average particle size in the range of about 0.1 micron to about 1 micron and a concentration of not greater than about 5%.

6. A lubricious polymeric catheter tube as recited in claim 3 wherein said zinc stearate has a concentration in the range of about 0.1% to 2.0%.

7. A lubricious polymeric catheter tube as recited in claim 3 wherein said molybdenum disulfide has an average particle size in the range of about 0.3 micron to about 40 microns and a concentration in the range of about 2% to about 8%, wherein said polytetrafluoroethylene particles have an average particle size in the range of about 0.1 micron to about 1 micron and a concentration of not greater than about 5%, and wherein said zinc stearate has a concentration in the range of about 0.1% to about 2.0%.

* * * * *

UNITED STATES PATENT AND TRADEMARK OFFICE
CERTIFICATE OF CORRECTION

PATENT NO : 6,086,970
DATED : July 11, 2000
INVENTOR(S) : Brooke Q. Ren

It is certified that error appears in the above-identified patent and that said Letters Patent are hereby corrected as shown below:

Column 7, claim 1, line 19, change "polytetrafluoroethylenc" to -- polytetrafluoroethylene--.

Signed and Sealed this

Tenth Day of April, 2001

*Attest:*

NICHOLAS P. GODICI

*Attesting Officer*     *Acting Director of the United States Patent and Trademark Office*